United States Patent
White et al.

(10) Patent No.: US 7,473,254 B2
(45) Date of Patent: Jan. 6, 2009

(54) PIVOTING BONE REAMER FOR MINIMALLY INVASIVE JOINT SURGERY

(75) Inventors: Patrick Michel White, Downington, PA (US); André Lechot, Orvin (CH); Yves Desarzens, Corgemont (CH); Hugh Davies, Lignieres (CH)

(73) Assignee: Precimed S.A., Orvin (CH)

( * ) Notice: Subject to any disclaimer, the term of this patent is extended or adjusted under 35 U.S.C. 154(b) by 726 days.

(21) Appl. No.: 10/431,908

(22) Filed: May 8, 2003

(65) Prior Publication Data

US 2003/0212402 A1    Nov. 13, 2003

(51) Int. Cl.
*A61B 17/00*    (2006.01)
(52) U.S. Cl. ......................................................... 606/81
(58) Field of Classification Search ................. 606/170, 606/180, 79–81
See application file for complete search history.

(56) References Cited

U.S. PATENT DOCUMENTS

| | | | | |
|---|---|---|---|---|
| 1,485,615 | A * | 3/1924 | Jones | 175/263 |
| 1,498,463 | A * | 6/1924 | McCloskey et al. | 175/285 |
| 2,548,724 | A * | 4/1951 | Jones | 175/263 |
| 3,702,611 | A | 11/1972 | Fishbein | |
| 4,811,632 | A | 3/1989 | Salyer | |
| 5,928,239 | A | 7/1999 | Mirza | |
| 7,048,740 | B2 * | 5/2006 | White et al. | 606/80 |
| 2003/0060889 | A1 * | 3/2003 | Tarabishy | 623/22.12 |

FOREIGN PATENT DOCUMENTS

| | | | | |
|---|---|---|---|---|
| DE | 38 40 466 | A | 6/1990 | |
| DE | 10148022 | * | 9/2001 | 606/86 |
| EP | 0 806 183 | A | 11/1997 | |
| SU | 982679 | | 12/1982 | |

OTHER PUBLICATIONS

The Standard Search Report in SN RS 109341.

* cited by examiner

*Primary Examiner*—Pedro Philogene
(74) *Attorney, Agent, or Firm*—Moetteli & Associates SARL

(57) ABSTRACT

A rotary surgical reamer assembly for removing bone and tissue from a joint to facilitate the installation of a prosthetic device. The assembly includes a hollow reamer body having an opening and a base portion. The base portion includes a first pivoting link member, a wall with a surface defining a central cavity, and a plurality of spaced apart cutting sites defining apertures through said wall. A shaft is configured to be de-mountably attached to a rotary source of power. The shaft has a rotary axis and a second pivoting link member coupled to the first pivoting link member. The axis of the shaft forms an angle to the base portion. A mechanism adjusts the angle of the hollow reamer body from an un-deployed position to a deployed position.

26 Claims, 9 Drawing Sheets

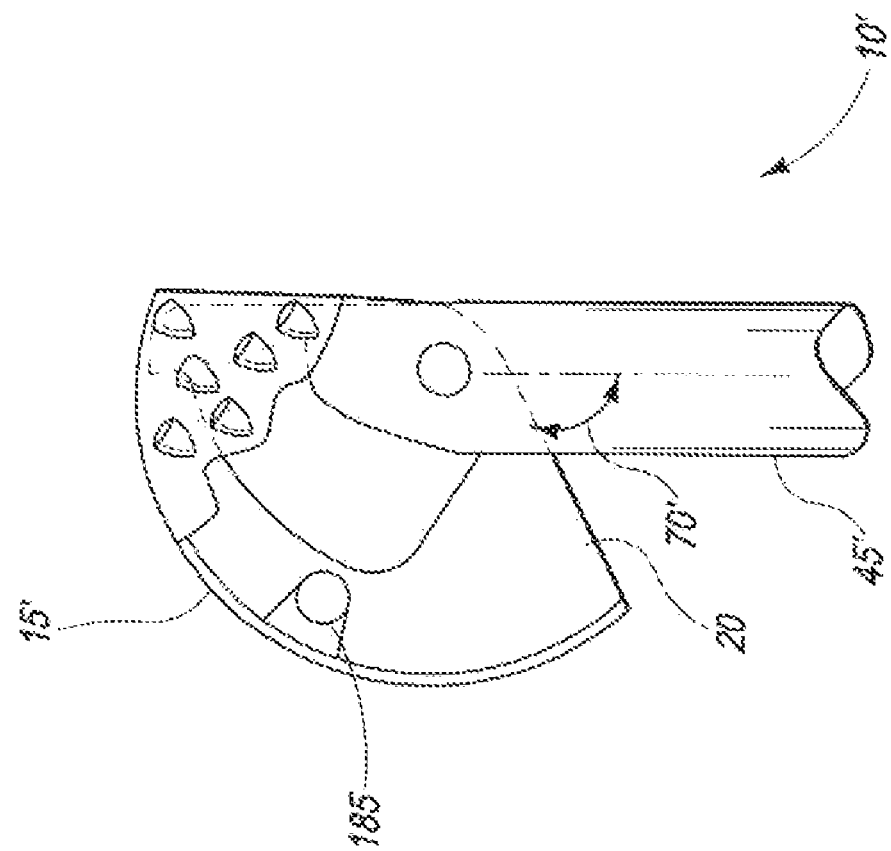
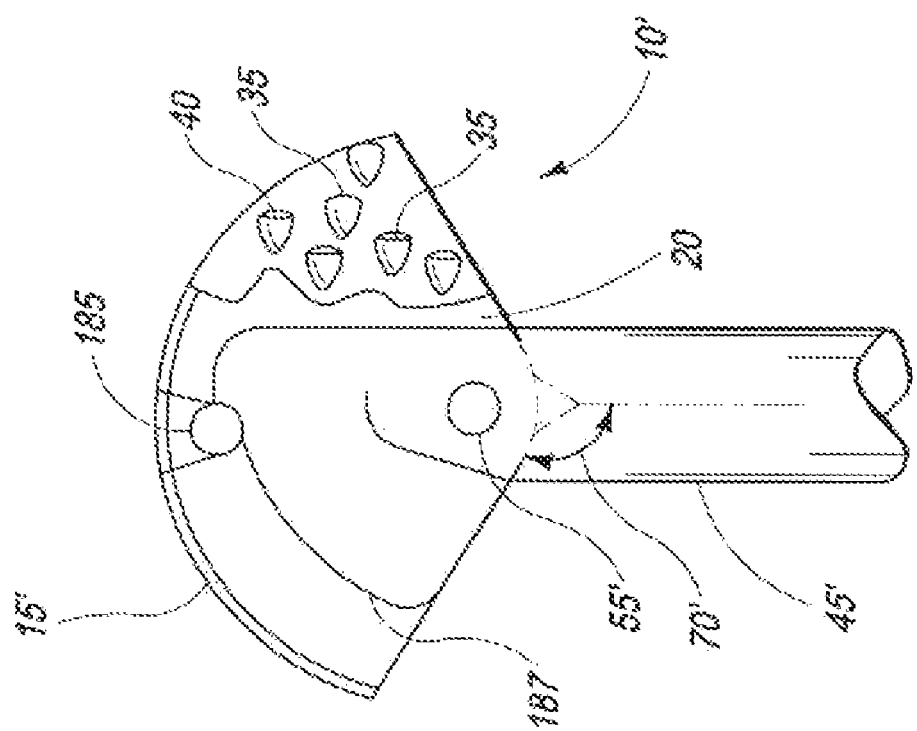

PIVOTING BONE REAMER FOR MINIMALLY INVASIVE JOINT SURGERY

BACKGROUND OF THE INVENTION

The present invention is a development and improvement to reamers of the type used in joint replacement surgery and in particular for the recently developing field of minimally invasive joint surgery.

Factors such as the perpetual pressure to improve the standard of patient care, the increasing costs of surgery, a population trend that has an increasing proportion of elderly persons suffering from osteoarthritis, have initiated change to the nature of joint replacement. The main areas of change in surgery have three primary goals: first, to minimize the trauma of surgery to individual patients; second, to diminish the time that the patient is required to remain in hospital after surgery; and third, to reduce the time of surgery. All of the above may be accomplished by reducing the size of incision, something often described as minimal access or minimal invasive joint surgery.

The smaller incision and the associated change in surgical technique that cuts fewer soft tissue structures reduces the injury to the patient caused by the operation and thereby allows a shorter recovery time. The procedure is may be made quicker in certain respects when a smaller incision is made, due to the lower number of blood vessels and soft tissue structures damaged. Further, fewer repairs are required when closing the incision after the joint replacement.

A consequence of a smaller incision is that it can be harder for the surgeon to have a clear view of the operative site. Further, implants and instruments pass closer to or are in fact touching the edges of the wound more often. This contact with the edges of the incision may create an associated risk of infection or of soft-tissue injury. To minimize this risk, a trend exists to make instruments smaller and smaller and/or of different geometries as described in pending applications Ser. Nos. PCT/IB01/02676, U.S. 60/372,285, and U.S. 60/376,479, of the assignee, all of which are fully incorporated herein and relied on.

One approach at minimizing the injury to the patient during such bone operations has been to reduce the width of the front profile of a standard acetabular reamer (which has also been referred to as the static profile in the referenced cases cited immediately above) so that the reamer can pass more easily through a smaller incision. However, such designs generally compromise the cutting surface of the reamer in that there are less cutting sites available for the purpose of cutting bone.

What is needed therefore, is a tool for use in performing minimally invasive surgery having a large dynamic profile while not compromising the total number of cutting sites on the tool.

SUMMARY OF THE INVENTION

A rotary surgical reamer assembly is provided which meets the needs identified above. The reamer assembly removes bone and tissue from a joint to facilitate the installation of a prosthetic device and includes a hollow reamer body having an opening and a base portion. The base portion includes a first pivoting link member, a wall with a surface defining a central cavity, and a plurality of spaced apart cutting sites defining apertures through said wall. A shaft is mountable to the hollow reamer body and is configured to be de-mountably attached to a rotary source of power. The shaft has a rotary axis and a second pivoting link member coupled to the first pivoting link member. The axis of the shaft forms an angle to the base portion. A mechanism adjusts the angle to the base portion of the hollow reamer body from an un-deployed position to a deployed position.

The bone reamer of the invention provides for entry of the reamer on its side profile and then for pivoting the reamer into place for use. The pivoting reamer thus presents an incision with a small profile upon insertion through the incision. Once pivoted into place, the assembly then presents the bone with a full hemispherical reamer for effective cutting.

The surgeon can manipulate the reamer using a reamer handle. The function of this manipulation is to act as a bridge between the power tool and the reamer which can transmit the applied torque to cut the bone. These reamer handles can be specially designed to not impinge the skin during use as shown in U.S. 60/376,479, entitled Reamer Spindle for Minimally Invasive Joint Surgery.

In another embodiment of the invention, the assembly is constructed from a partially spherical hollow reamer body having an opening and an axel spanning the opening. In this embodiment, the shaft has a first gear attached to the other end and a pivoting link member coupled to the axel with the axis forming an angle to the base portion. There is a second drive gear which interacts with the first gear and the reamer dome to adjust the angle of the reamer from an un-deployed position to a deployed position. Of course, the placement of the first and second drive gears may be reversed.

It is an advantage of the present invention that the acetabular reamer be inserted in an un-deployed position with its side profile passing through the incision, due to the fact that the side profile is smaller than its dynamic cutting profile.

It is another advantage that the reamer pivots into place in a deployed position for reaming bone.

It is yet another advantage that a simple mechanism be used to pivot the reamer between a deployed and an un-deployed position.

BRIEF DESCRIPTION OF THE DRAWINGS

The attached drawings represent, by way of example, embodiments of the subject of the invention.

FIG. 7A is a partial cross-sectional side view of an alternative embodiment of the present invention showing a gear mechanism in a deployed position.

FIG. 7B is a partial cross-sectional side view of the alternative embodiment of the present invention showing a gear mechanism in an un-deployed position.

DETAILED DESCRIPTION OF THE DRAWINGS

Figure 1:
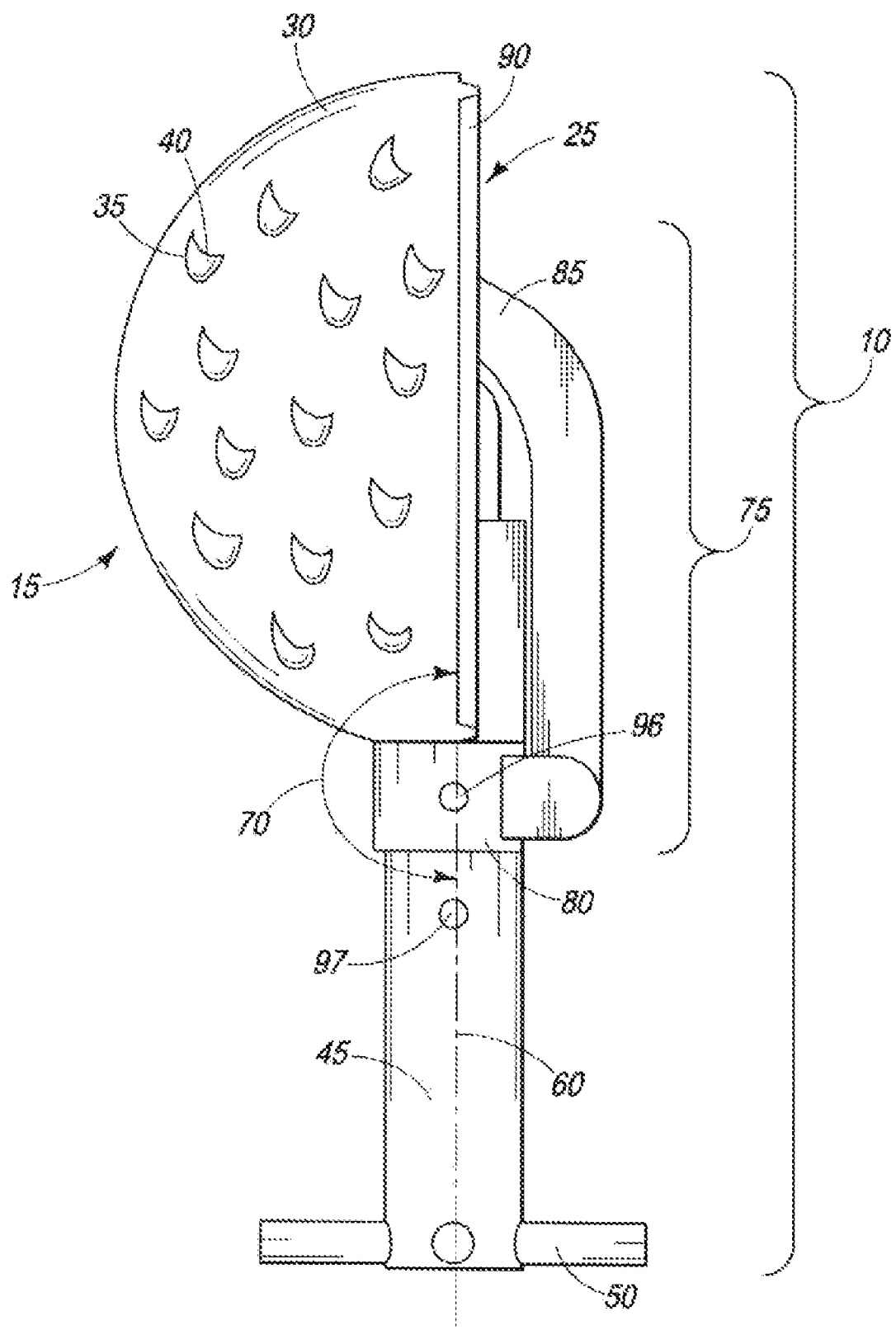
FIG. 1 is a side view of the pivoting reamer of the present invention in an un-deployed position.
Figure 2:
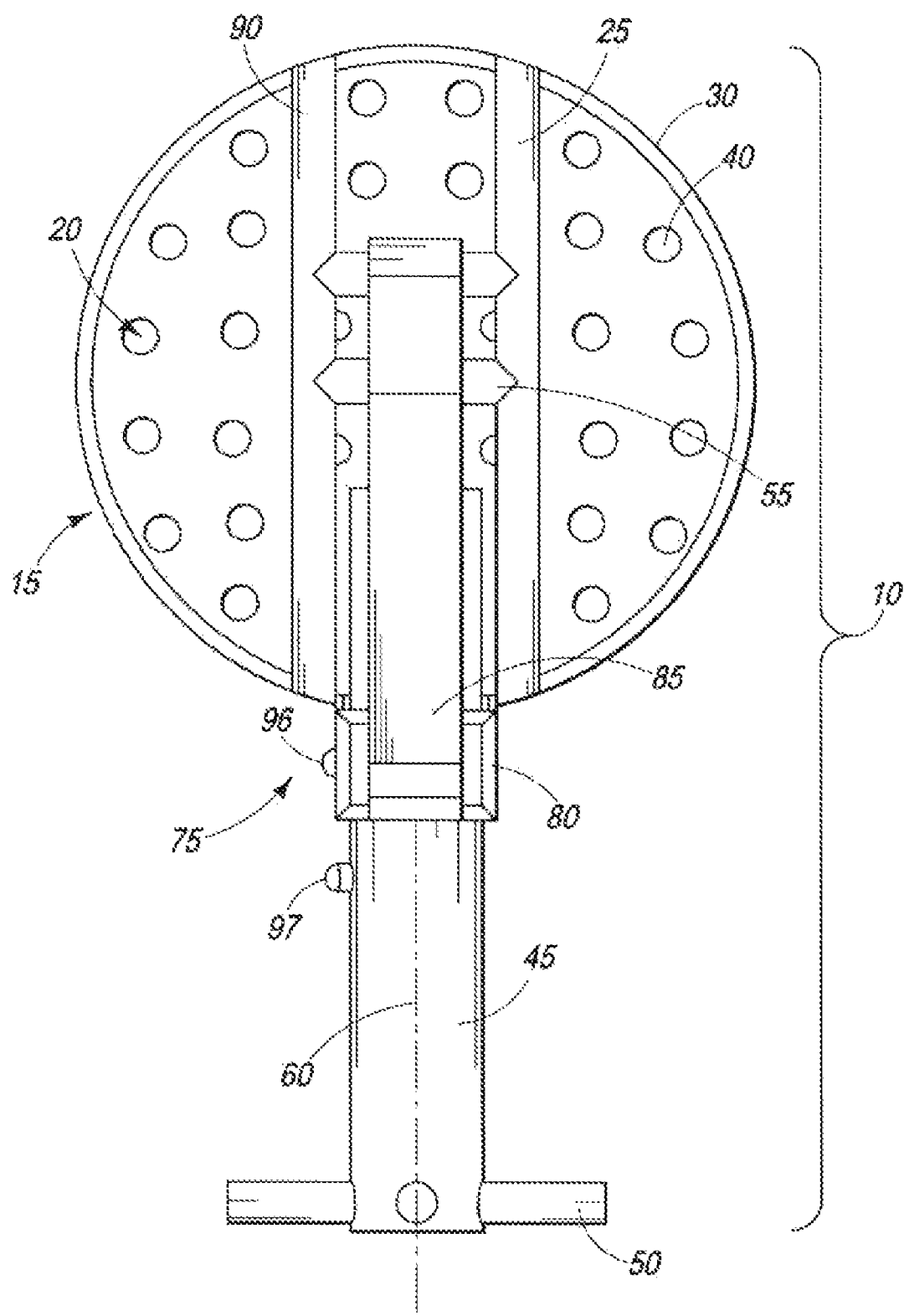
FIG. 2 is a rear view of the pivoting reamer of the present invention in an un-deployed position.
Figure 3:
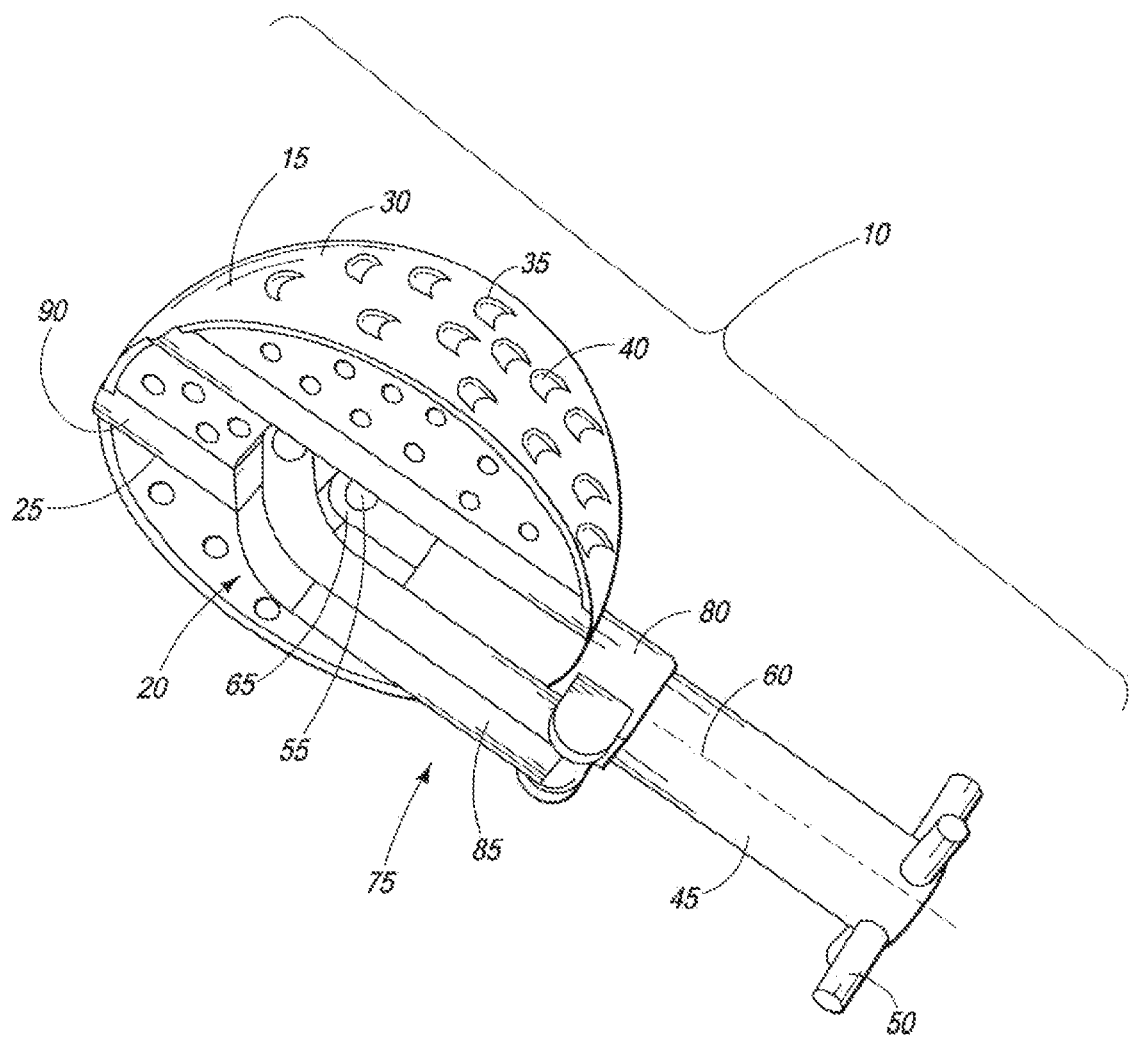
FIG. 3 is a perspective view of the pivoting reamer of the present invention in an un-deployed position.
Figure 4:
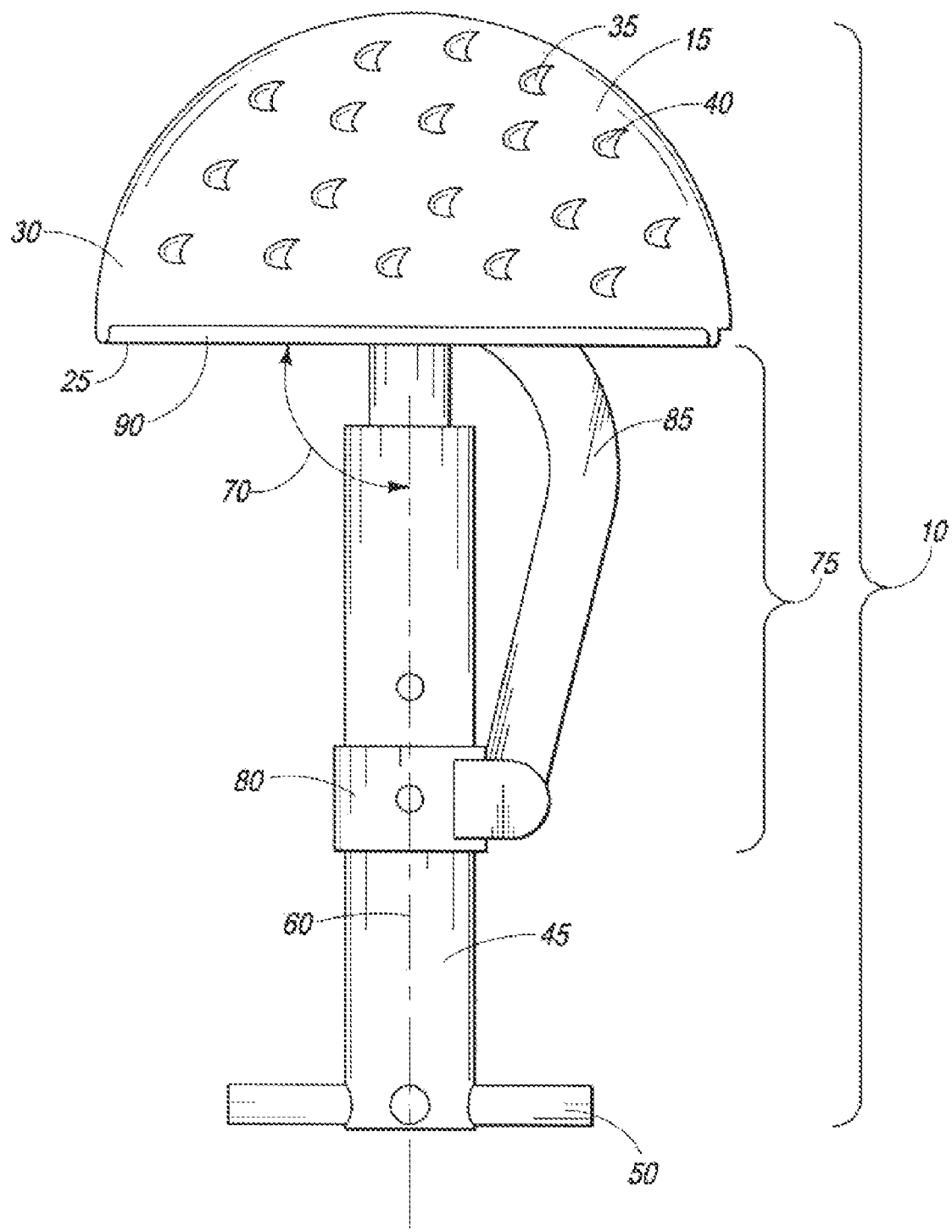
FIG. 4 is a side view of the pivoting reamer of the present invention in a deployed position.
Figure 5:
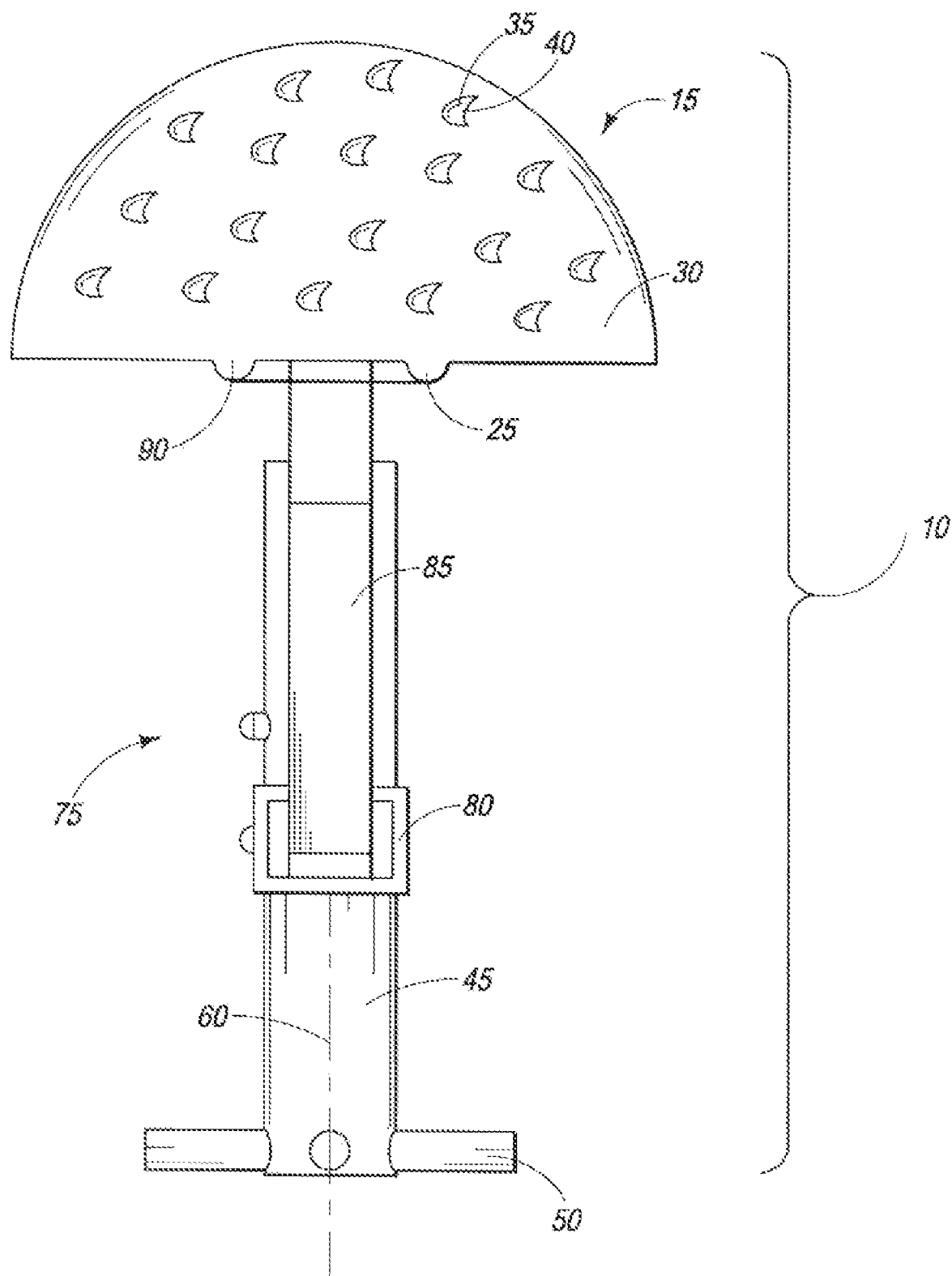
FIG. 5 is a rear view of the pivoting reamer of the present invention in a deployed position.
Figure 6:
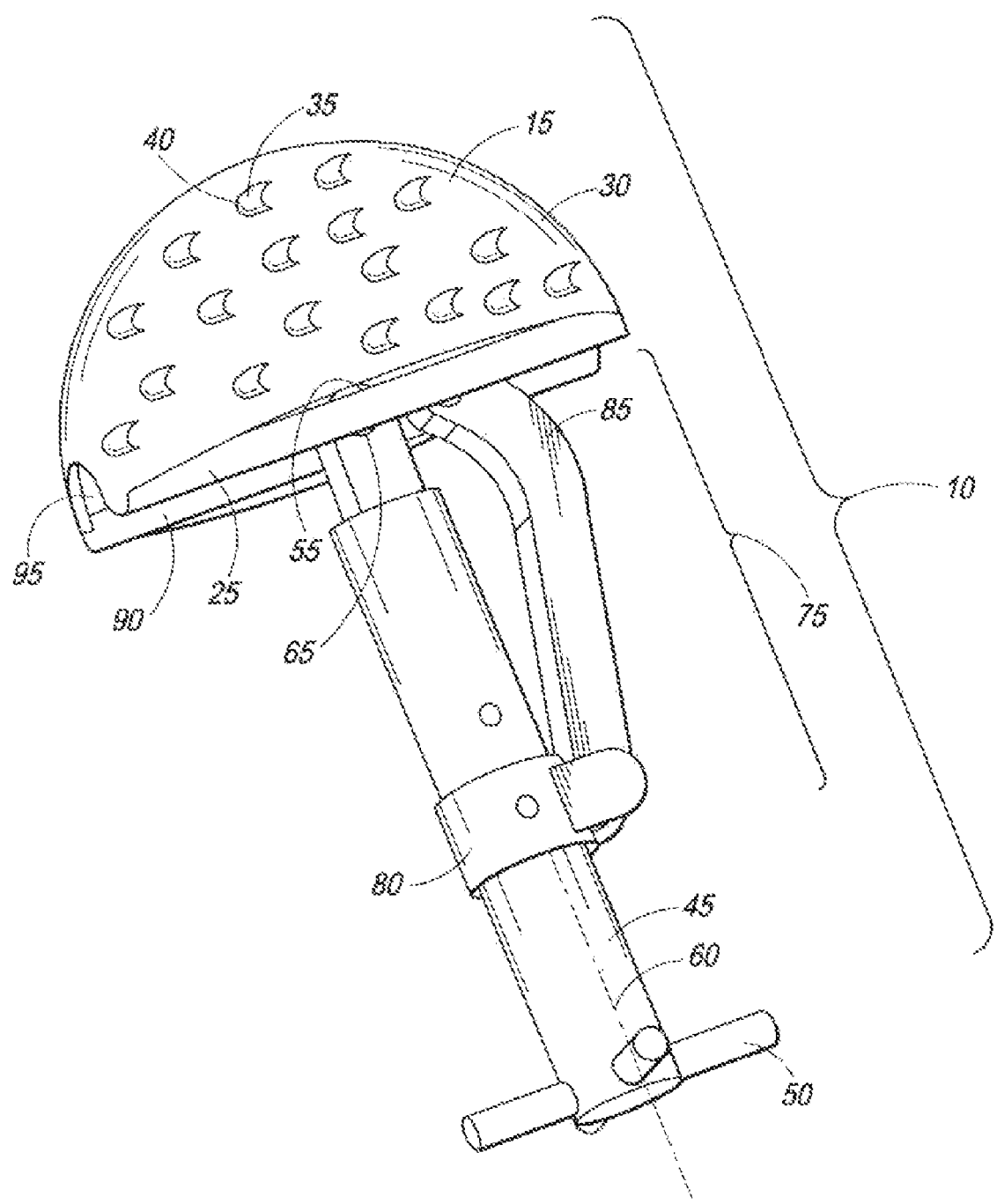
FIG. 6 is a perspective view of the pivoting reamer of the present invention in a deployed position.

Referring to FIGS. 1-8 a surgical reamer assembly in the form of an acetabular reamer assembly 10 is generally shown, with a hollow reamer body 15 in the shape of a section of a sphere. The hollow reamer body 15 has an opening 20 and a base portion 25 which is generally shown. The reamer body 15 has a wall 30 with spaced apart cutting sites 35 defining apertures 40 through the wall 30 through which cut bone and tissue may pass for removal from the cutting site. The base portion 25 includes a first pivoting link member in the form of an axel 55. A rotary source of power is not shown; however the shaft 45 is adapted with an interface 50 as shown in FIGS. 1-6 for connecting to this source of power. Any suitable means of interfacing with power (a drill, another shaft, or the surgeon's hand) would be acceptable as a replacement for the interface 50 shown. The shaft 45 is configured with a rotary axis 60 and has a second pivoting joint 65 as shown in FIG. 3 which is coupled to the axel 55 with the axis 60 forming an angle 70 with the base 25 as shown in FIGS. 1 and 4. A mechanism 75 is generally shown for adjusting the angle 70 from an un-deployed position as shown in FIGS. 1-3 to a deployed position as shown in FIGS. 4-6. This mechanism can be limited to a set range of angular adjustability or be freely adjusted by the surgeon. Stops can be provided to hold the reamer at set angular relationships if the surgeon desires.

Referring more closely to FIGS. 1-6, the mechanism 75 of the acetabular surgical reamer assembly 10 includes a sleeve 80 slideable along the axis 60. The mechanism 75 also includes a linkage 85. The base portion 25 is preferably shown with at least one but preferably two bars 90 spanning the opening 20. In this first embodiment, the base portion 25 includes the axel 55 which is connected to the linkage 85 with the second pivoting link member 65. The surgeon may slide the sleeve 80 along axis 60 which moves the linkage 85 to adjust the angle 70 from an un-deployed position which is useful for insertion into the smaller incision as shown in FIGS. 1-3 to a deployed position as shown in FIGS. 4-6 preparing the reamer to cut the acetabular socket. A notch 95 is provided to allow the shaft 45 to be recessed into the partially spherical hollow reamer body 15 in an un-deployed position to minimize its size as it is inserted through the incision. A detent stop 96 is provided to lock the acetabular reamer assembly 10 in the un-deployed position while inserting it through the incision. Another detent stop 97 is provided to lock the acetabular reamer assembly 10 in the deployed position preparing it for use after being inserted through the incision. With this device, the surgeon can easily adjust the angle 70 for insertion and reposition the hollow reamer body 15 for cutting.

Referring now to FIGS. 7A-7B, an alternate embodiment 10' of an acetabular surgical reamer 10 is shown. In this embodiment, the mechanism 75' includes a drive gear 185 which interacts with a first gear 187 and the partially spherical hollow reamer body 15'. A shaft 45' carries the first gear 187 and a pivoting link member (not shown). The pivoting link member 55' is coupled with the base 25' which is shown as an axel 55' spanning the opening 20'. Unlike FIGS. 1-6, this axel 55' and the base 25' are the same member. As the drive gear 185 is activated, it interacts with first gear 187 to move the hollow reamer body from an un-deployed position as shown in FIG. 7B to a deployed position as shown in FIG. 7A. As with other embodiments, the surgeon can easily adjust the angle 70' for insertion and reposition the partially spherical hollow reamer body 15' for cutting. Note that the drive gear 185 can be driven in any number of way, including by a band and/or a drive train housed primarily in the reamer body.

Figure 8B:
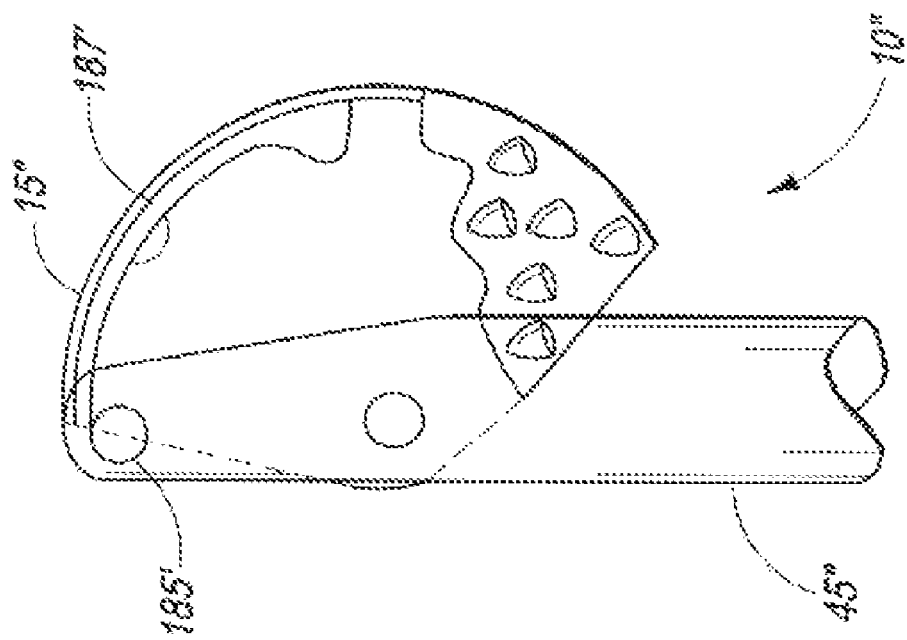
FIGS. 8A and 8B are partial cross-sectional side views of another alternative embodiment of the invention in a deployed and undeployed position, respectively, in which the positions of the gears of FIGS. 7A-7B are reversed.
Figure 8A:
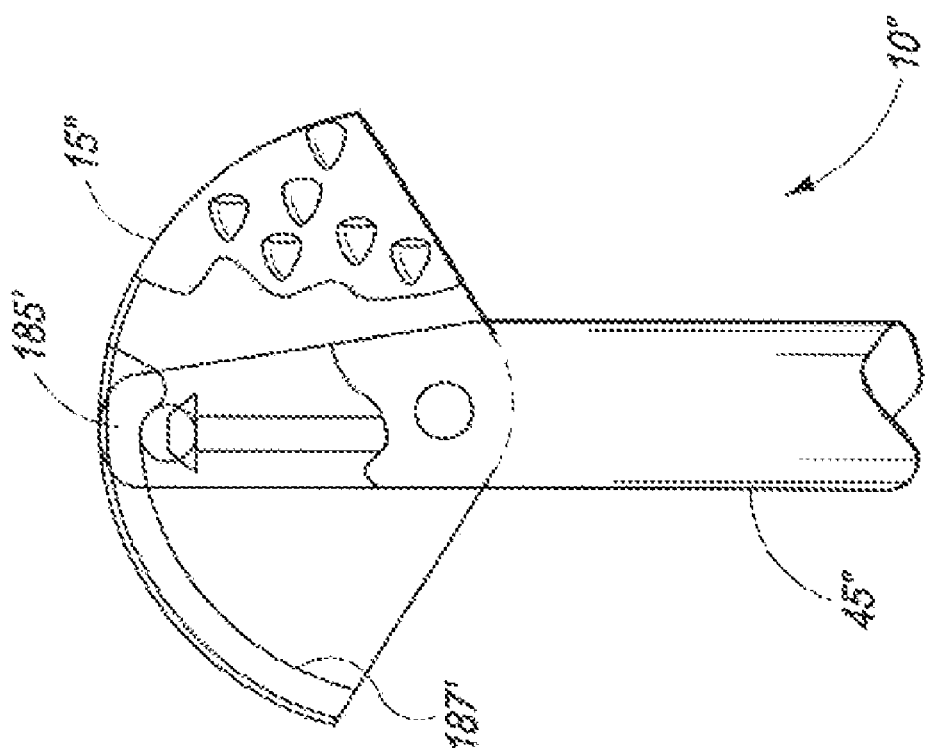

Referring now to FIGS. 8A-8B, a third embodiment 10" is shown, in which, essentially, the positions of the drive gear 185 and the gear 187 are reversed, so that a gear 187' is attached to the inner surface of the reamer body 15", and a drive gear 185' is fixed to be driven at the tip of the shaft 45'". Note that offsetting the position of the drive gear 185' from center allows the gear to be better concealed under the reamer body 15" both in the insertion and cutting positions of the reamer body. It should be noted that the gear 187' attached to the inner surface of the reamer body 15 may be substituted with a simple series of perforations (not shown) in the reamer body, into which the gear teeth of the drive gear 185' may enter, thereby driving the reamer body from a cutting to an insertion position. Note that the portions of FIGS. 7A to 8B having a heavier line weight indicate a pitch line along which teeth (not shown) are disposed. This embodiment has the advantage that the drive is simpler, and that the reamer body need not include the complication of a drive train, and thus can be inexpensively manufactured.

Figure 9B:
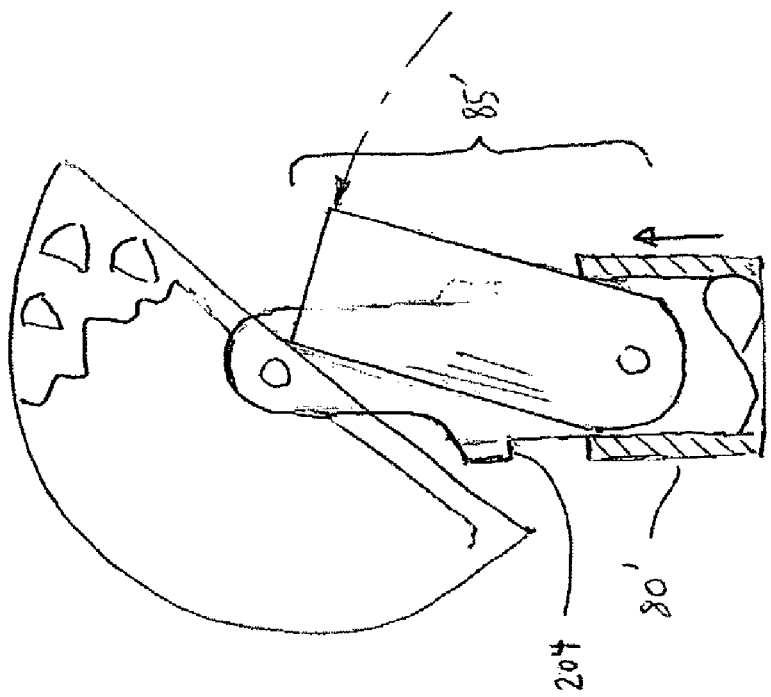
FIGS. 9A and 9B are partial cross-sectional side views of another embodiment of the invention in a deployed and undeployed position, respectively, using a cam lock mechanism.
Figure 9A:
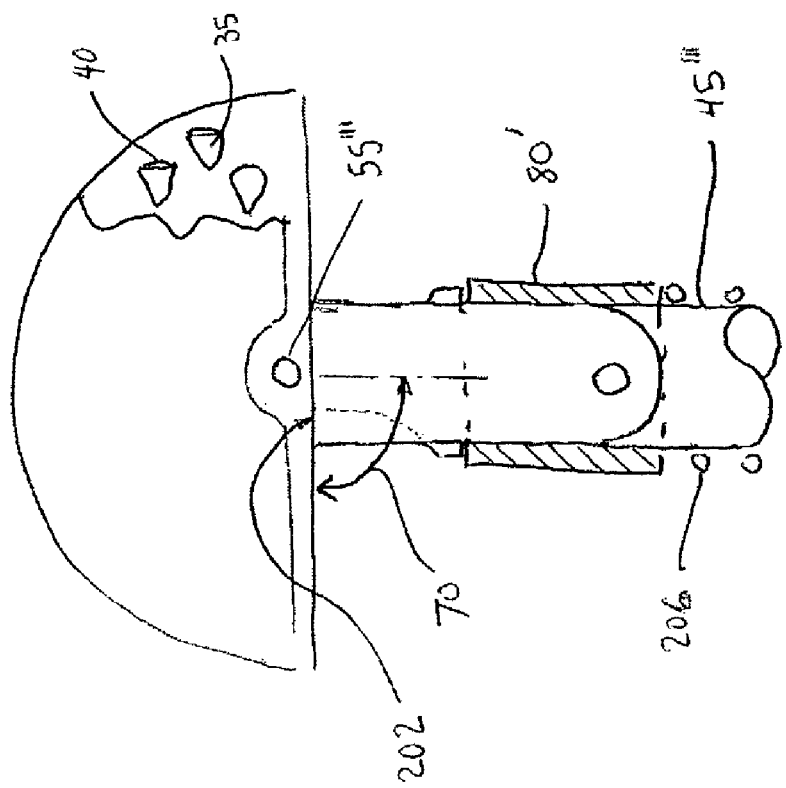

Referring now to FIGS. 9A and 9B, an embodiment 10'" is shown in which the linkage 85 is substituted for a cam mechanism 85'. The cam mechanism 85' includes a pivoting cam 200 which is urged along cam surface 202 when a sleeve 80' moves up along the axis of the shaft 45'". The sleeve 80' is urged into a locked position against a stop 204 by a spring 206.

The rotary surgical reamer assembly 10, 10', or 10" of the invention is useful for removing bone and tissue from a joint socket when performing reconstructive surgery, to facilitate the installation of a prosthetic device or to repair the damaged bone.

It is an advantage of the present invention that the acetabular reamer assembly 10, 10', or 10" be inserted in an un-deployed position with its side profile passing through the incision, due to the fact that the side profile is smaller than its dynamic cutting profile.

It is another advantage that the reamer assembly 10, 10', or 10" pivots into place in a deployed position for reaming bone.

It is yet another advantage that a simple mechanism 75, 75', or 75" be used to pivot the reamer between a deployed and an un-deployed position.

Multiple variations and modifications are possible in the embodiments of the invention described here. Although certain illustrative embodiments of the invention are shown and described here, a wide range of modifications, changes, and substitutions is contemplated in the foregoing disclosure. In some instances, certain features of the present invention may be employed without a corresponding use of the other features. Accordingly, it is appropriate that the foregoing description be construed broadly and understood as being given by way of illustration and example only, the spirit and scope of the invention being limited only by one, another or a further aspect of the appended claims.

What is claimed is:

1. A rotary surgical reamer assembly for removing bone and tissue from a bone joint to facilitate the installation of a prosthetic device, the assembly comprising a rotatable reamer body connected to a drive shaft, wherein the reamer body is pivotably adjustable with respect to the drive shaft from an insertion position to a cutting position, the insertion position of which having a smaller static insertion profile than the cutting position in order to minimize trauma of a patient upon insertion through an incision and/or through soft tissue wherein the reamer body has an opening and a base portion including a first link member, a wall with a surface defining a central cavity, and a plurality of spaced apart cutting sites defining apertures through the wall, wherein the shaft of the reamer assembly has a rotary axis and a second link member adapted for coupling with the first link member with the axis forming an angle to the base portion, and wherein the assembly further has a mechanism for adjusting the angle to the base portion of the hollow reamer body from an un-deployed position to a deployed position.

2. The surgical reamer assembly of claim 1, wherein the reamer body is in the form of a section of a sphere.

3. The surgical reamer assembly of claim 2, wherein the reamer body is an acetabular reamer.

4. The surgical reamer assembly of claim 1, wherein the base portion is comprised of at least one bar spanning the opening of the hollow reamer body.

5. The surgical reamer assembly of claim 4, having a second bar offset from the at least one bar.

6. The surgical reamer assembly of claim 5, wherein the bar includes an axle for connecting the reamer body and the second link member together.

7. The surgical reamer assembly of claim 1, wherein the mechanism for adjusting the angle of the hollow reamer body from an un-deployed position to a deployed position comprises a sleeve slideable along the axis.

8. The surgical reamer assembly of claim 7, wherein the shaft presents a locking stop for engaging the sleeve in its deployed position.

9. The surgical reamer assembly of claim 1, wherein the mechanism is a linkage.

10. The surgical reamer assembly of claim 1, wherein the mechanism is a cam.

11. The surgical reamer assembly of claim 4, wherein the bar and the first link member are integral, connecting the second link member to the hollow reamer body.

12. The surgical reamer of claim 4, wherein the first and second link members are offset from one another and the second link member pivotally connects between the first link member and a sleeve which slides along the axis.

13. The surgical reamer assembly of claim 11, wherein the mechanism comprises a gear.

14. An acetabular surgical reamer assembly for removing bone and tissue from a hip joint to facilitate the installation of a prosthetic device, the assembly comprising:
(a) a hollow reamer body having an opening and a base portion spanning the opening including an axel, a wall with a surface defining a central cavity and a plurality of spaced apart cutting sites defining apertures through said wall,
(b) a shaft configured to be de-mountably attached to a rotary source of power, the shaft having a rotary axis and a link member coupled to the axel with the axis forming an angle to the base portion, and
(c) a linkage for adjusting the angle to the base portion of the hollow reamer body from an un-deployed position to a deployed position.

15. The surgical reamer assembly of claim 14, wherein a component of the mechanism for adjusting the angle of the hollow reamer body from an un-deployed position to a deployed position is a sleeve slideable along the axis.

16. The surgical reamer assembly of claim 15, wherein the shaft presents a locking stop for engaging the sleeve in its deployed position.

17. The surgical reamer assembly of claim 15, wherein one end of the linkage is pivotally attached to the sleeve and the other end is pivotally attached to the base of the reamer body at a pivot point offset from the first link member.

18. An acetabular surgical reamer assembly for removing bone and tissue from a hip joint to facilitate the installation of a prosthetic device, the assembly comprising:
(a) a hollow reamer body having an opening and a first link member comprising an axel spanning the opening, a wall with a surface defining a central cavity and a plurality of spaced apart cutting sites defining apertures through said wall,
(b) a shaft configured to be de-mountably attached to a rotary source of power, the shaft carrying a second link member comprising a first gear with the axis forming an angle to the base portion, and
(c) a drive gear interacting with the second linking member to adjust the angle of the hollow reamer body from an un-deployed position to a deployed position.

19. A rotary surgical reamer assembly for removing bone and tissue from a bone joint to facilitate the installation of a prosthetic device, the assembly comprising a rotatable reamer body connected to a drive shaft, wherein the reamer body is pivotably adjustable with respect to the drive shaft from an insertion position to a cutting position, the insertion position of which having a smaller static insertion profile than the cutting position in order to minimize trauma of a patient upon insertion trough an incision and/or through soft tissue, the reamer assembly further comprising a rotatable reamer body, wherein the reamer body is in the form of a section of a sphere, the rotatable reamer body further comprising a base portion and an opening including a first link member, wherein the base portion comprises at least one bar spanning the opening of the hollow reamer body, further comprising a second bar offset from the at least one bar, the drive shaft further comprising a rotary axis and a second link member adapted to couple with the first link member with the axis forming an angle to the base portion, wherein the bar includes an axle for connecting the reamer body and the second link member together.

20. The surgical reamer assembly of claim 19, further comprising a mechanism for adjusting the angle to the base portion of the hollow reamer body hum an un-deployed position to a deployed position, wherein the mechanism comprises a sleeve slideable along the axis.

21. The surgical reamer assembly of claim 20, wherein the drive shaft presents a locking stop for engaging the sleeve in its deployed position.

22. The surgical reamer assembly of claim 20, wherein the mechanism is a linkage.

23. The surgical reamer assembly of claim 20, wherein the mechanism is a cam.

24. The surgical reamer assembly of claim 19, wherein the bar and the first link member are integral, connecting the second link member to the hollow reamer body.

25. The surgical reamer of claim 19, wherein the first and second link members are offset from one another and the second link member pivotally connects between the first link member and a sleeve which slides along the axis.

26. The surgical reamer assembly of claim 24, wherein the mechanism composes a gear.

* * * * *

UNITED STATES PATENT AND TRADEMARK OFFICE
CERTIFICATE OF CORRECTION

PATENT NO.        : 7,473,254 B2  
APPLICATION NO. : 10/431908  
DATED             : January 6, 2009  
INVENTOR(S)       : Patrick Michel White et al.

It is certified that error appears in the above-identified patent and that said Letters Patent is hereby corrected as shown below:

In Col. 6, line 41, replace the phrase "body hum an un-deployed posi-" with --body from an un-deployed posi- --.

Signed and Sealed this

Twenty-fourth Day of March, 2009

JOHN DOLL  
*Acting Director of the United States Patent and Trademark Office*